(12) United States Patent
Larson et al.

(10) Patent No.: US 11,154,865 B2
(45) Date of Patent: Oct. 26, 2021

(54) MICROFLUIDIC DEVICE

(71) Applicant: Lariat Biosciences, Inc., Beverly, MA (US)

(72) Inventors: Jonathan W. Larson, Chelsea, MA (US); Alexandra Damiano, Sturbridge, MA (US)

(73) Assignee: Lariat Biosciences, Inc., Beverly, MA (US)

( * ) Notice: Subject to any disclaimer, the term of this patent is extended or adjusted under 35 U.S.C. 154(b) by 189 days.

(21) Appl. No.: 16/331,051

(22) PCT Filed: Sep. 6, 2017

(86) PCT No.: PCT/US2017/050241
§ 371 (c)(1),
(2) Date: Mar. 6, 2019

(87) PCT Pub. No.: WO2018/048876
PCT Pub. Date: Mar. 15, 2018

(65) Prior Publication Data
US 2019/0217299 A1    Jul. 18, 2019

Related U.S. Application Data

(60) Provisional application No. 62/383,887, filed on Sep. 6, 2016.

(51) Int. Cl.
*B01L 3/00* (2006.01)
*G01N 27/447* (2006.01)
(Continued)

(52) U.S. Cl.
CPC .......... *B01L 3/502784* (2013.01); *C12Q 1/68* (2013.01); *G01N 27/416* (2013.01); *G01N 27/447* (2013.01); *B01L 2300/0645* (2013.01)

(58) Field of Classification Search
CPC ....... B01L 2300/0645; B01L 3/502784; C12Q 1/68; G01N 27/416; G01N 27/447
See application file for complete search history.

(56) References Cited

U.S. PATENT DOCUMENTS

2011/0114190 A1    5/2011    Wen et al.
2016/0136643 A1*   5/2016    Larson ................ B01F 13/0071
                                                          506/2

FOREIGN PATENT DOCUMENTS

WO    WO-2012/027366 A2    3/2012
WO    WO-2014/145555 A1    9/2014
(Continued)

OTHER PUBLICATIONS

International Search Report and Written Opinion for International Application No. PCT/US2017/050241 dated Feb. 7, 2018.

*Primary Examiner* — Jennifer Wecker
(74) *Attorney, Agent, or Firm* — Foley Hoag LLP

(57) ABSTRACT

In the invention described here, the conventional need for feedback control is eliminated by a passive, open-loop approach using a novel microfluidic droplet generator with a step enhancement. The invented droplet generator yields uniform droplet volumes over a wide range of operating pressures, delivering robust performance at a very low cost. The invention also describes a method of droplet generation whereby the step enhancement improves the performance of any squeeze-mode or dripping-mode droplet generator, including but not limited to bridge-mode and flow-focusing configurations. The performance of the invention is sufficiently stable that it can be operated manually yet still deliver best-in-class microfluidic performance. Thus, not only does the invention greatly simplify and reduce the cost of operation in the laboratory, it opens the possibility of performing precision biology out in the field and off of the electrical grid.

20 Claims, 7 Drawing Sheets

(51) Int. Cl.
*G01N 27/416* (2006.01)
*C12Q 1/68* (2018.01)

(56) References Cited

FOREIGN PATENT DOCUMENTS

| WO | WO-2014/153071 A1 | 9/2014 |
| WO | WO-2015/195698 A1 | 12/2015 |

\* cited by examiner

MICROFLUIDIC DEVICE

CROSS-REFERENCE

This application is a national stage filing under 35 U.S.C. § 371 of PCT/US17/50241, filed on Sep. 6, 2017, which claims the benefit of U.S. Provisional Application No. 62/383,887, filed Sep. 6, 2016, the entirety of which are hereby incorporated by reference.

BACKGROUND

Microfluidic droplet generators are capable of producing continuous streams of very uniformly sized droplets over short periods of time. Common applications for droplet generators include cell encapsulation, directed evolution, single biomolecule analysis, droplet digital PCR, and single-cell gene expression profiling. Each of these applications takes strong advantage of the high degree of uniformity in droplet volume. However, droplet volumes can drift significantly over the course of a single run, often requiring active feedback control of flow rates to stabilize droplet volume for longer durations. A major cause of size drift is variation in flow rate due to either pulsation from syringe pumps or sawtooth pressure profiles from gas regulators. Generally, feedback control on droplet size relies on expensive machine vision systems that can dominate the overall cost of the instrumentation.

SUMMARY

Provided herein is a method comprising:
providing a system, the system comprising a substrate that defines microfluidic channels including:
  a main channel having a main input in fluid communication with a main output, the main channel defining an intersection site along a path of fluid flow from the main input to the main output;
  a first side channel having a first side input in fluid communication with a first side output, the first side output being in fluid communication with the main channel at the intersection site;
  a second side channel having a second side input in fluid communication a second side output, the second side output being in fluid communication with the main channel at the intersection site;
  a first electrode located so as to be in electrical contact with the first side channel fluid when the first side channel has been charged with the first side channel fluid; and
  a second electrode located so as to be in electrical contact with the second side channel fluid when the second side channel has been charged with the second side channel fluid;
charging the main channel with a main channel fluid from the main input;
charging the first side channel with a first side channel fluid from the first side input, the first side channel fluid being immiscible with at least a first component of the main channel fluid;
charging the second side channel with a second side channel fluid from the second side input such that the first and second side channels are separated from one another by the main channel fluid, the second side channel fluid being immiscible with at least the first component of the main channel fluid;
flowing the main channel fluid from the main channel input to the main channel output and through the intersection point;
allowing electrical current to flow through the intersection;
connecting the first and second side channel fluids with a fluid bridge at the intersection point;
straining the fluid bridge within the main channel fluid such that the fluid bridge encounters at least one enhancement channel located downstream, within, or adjacent to the intersection site;
flowing the fluid bridge into the at least one enhancement channel, wherein said enhancement channel causes an abrupt drop in capillary pressure to thereby improve stability of droplet generation; and
disconnecting the fluid bridge from the first and second side channel fluids yielding a droplet and separating the first and second side channel fluids by the first component of the main channel fluid.

In some embodiments, the fluid bridge consists of a second component of the main channel fluid, wherein the second component is a dispersed aqueous droplet.

In some embodiments, the first and second side channel fluids are miscible with each other.

In some embodiments, the fluid bridge is miscible with both the first and second side channel fluids.

In some embodiments of the systems herein, connecting the first and second side channel fluids with the fluid bridge comprises forming an electrically conductive connection between the first and second side channel fluids.

In some embodiments, the system further comprises a voltage source connected to both the first electrode and the second electrode.

In some embodiments, the first electrode is located within the first side channel; and the second electrode is located within the second side channel.

In some embodiments, the first side channel fluid, the second side channel fluid and the fluid bridge are all aqueous.

In some embodiments, the first component of the main channel fluid is an oil.

In some embodiments, the fluid bridge consists essentially of the first and second side channel fluids, and contains substantially none of the first component of the main channel fluid.

In some embodiments of the methods herein, connecting the first and second side channel fluids with a fluid bridge comprises extending the first and second side channel fluids into the intersection site so that the first and second fluids come into contact, thereby forming the fluid bridge.

In some embodiments of the methods herein, disconnecting the fluid bridge from the first and second side channel fluids creates a droplet consisting essentially of the first and second side channel fluids.

In some embodiments, the system further comprises a current meter operably connected to the first and second electrodes so as to be capable of measuring the current between the first and second electrodes as a function of time; and the method further comprises recording the current measured by the current meter as a function of time.

In some embodiments, the fluid bridge is a second component of the main channel fluid; and flowing the main channel fluid comprises flowing the fluid bridge from the main channel input to the intersection point and from the intersection point to the main channel output.

In some embodiments, the system further comprises a current meter operably connected to the first and second electrodes so as to be capable of measuring the current between the first and second electrodes as a function of time; and the method further comprises recording the current measured by the current meter as a function of time.

In some embodiments of the methods herein, connecting the first and second side channel fluids with the fluid bridge comprises incorporating at least some of the first and/or second side channel fluids into the fluid bridge; and disconnecting the fluid bridge comprises retaining in the resulting droplet the incorporated at least some of the first and/or second side channel fluids.

In some embodiments, the second side channel defines (a) a second side current channel and (b) a second side pressure channel; the second side current channel and the second side pressure channel are both in fluid communication with the input port; the second side current channel and the second side pressure channel are contiguous at a second side intersection point in the second side channel; the second side electrode is positioned within the second side current channel; and the second pressure source is positioned in the second side pressure channel.

In some embodiments, the fluid flow path from the second side intersection point to the second side electrode is substantially different in length, cross-sectional area, or both length and cross-sectional area than the fluid flow path from the second side intersection point to the second pressure source.

In some embodiments, the fluid flow path from the second side intersection point to the second side electrode is substantially similar to the fluid flow path from the second side intersection point to the second pressure source.

In some embodiments, the second side channel includes a third side input in fluid communication with the second side output.

In some embodiments, the method further comprises charging the second side channel with a third side channel fluid from the third side input.

In some embodiments, the first side channel fluid includes a bead attached to a hybridization capture agent complementary to a predetermined nucleic acid sequence.

In some embodiments, said at least one enhancement channel distance to intersection channel width comprises a step offset ratio of 0, 0.1, 0.2, 0.5, 1.0, 2.0, 3.0, 4.0, or 5.0.

In some embodiments, said at least one enhancement channel is located downstream from the intersection channel.

In some embodiments, said at least one enhancement channel comprises a channel height that is larger than the intersection channel height.

In some embodiments, said at least one enhancement channel comprises a channel height that is 0.5×, 1×, 1.5×, 2×, 2.5×, 3×, 3.5×, 4×, 4.5×, and 5× larger than the intersection channel height.

In some embodiments, said at least one enhancement channel comprises a channel height that is from 1 µm to 500 µm.

In some embodiments, said at least one enhancement channel comprises a channel height that is 1, 2, 5, 10, 20, 50, 100, or 500 µm.

In some embodiments, the intersection channel comprises a channel height that is from 0.5 µm to 200 µm.

In some embodiments, said intersection channel comprises a channel height that is 0.5, 1, 2, 5, 10, 20, 50, 100, 200 µm.

In some embodiments, said at least one enhancement channel comprises a channel height of 50 µm.

In some embodiments, the intersection channel comprises a channel height of 20 µm.

In some embodiments, the systems herein comprise at least two, at least three, at least four, or at least five enhancement channels.

In some embodiments, the systems herein comprise one enhancement channel.

Another aspect of the invention is directed to a method comprising:
providing a system, the system comprising a substrate that defines microfluidic channels including:
an intersection site comprising a microfluidic droplet generator;
a first channel or set of channels having at least a first input in fluid communication with the intersection site;
a second channel or set of channels having at least a second input in fluid communication with the intersection site;
an exit channel or channels having an exit output in fluid communication with the intersection site;
charging the first channel or set of channels with at least a first channel fluid;
charging the second channel or set of channels with at least a second channel fluid, the first channel fluid being immiscible with the second channel fluid;
flowing the first channel fluid from the first channel input into the intersection site, and flowing the second channel fluid from the second channel input into the intersection site;
urging the first channel fluid into a strained pre-droplet by means of squeeze-mode or dripping-mode droplet generation within or downstream of the intersection site;
flowing the pre-droplet into at least one enhancement channel located downstream, within, or adjacent to the intersection site, wherein said enhancement channel causes an abrupt drop in capillary pressure to thereby improve stability of droplet generation; and
disconnecting the pre-droplet from the first channel fluid yielding a droplet.

In some embodiments, the first channel fluid is aqueous and the second channel fluid is an oil.

In some embodiments, the intersection site comprises a flow-focusing, head-on, T-junction, Y-junction, double T-junction, K-junction, V-junction, or co-flow droplet generators.

Another aspect of the invention is directed to a method of containing a species comprising encapsulating the species within a fluid droplet; then injecting into the fluid droplet reactants for gel polymerization; applying a high voltage to thereby merge droplets; then rigidifying the droplet by gel polymerization; and capturing the species within the rigidified droplet during polymerization.

In some embodiments, the injecting step comprises any of the methods described herein.

In some embodiments, injecting comprises microfluidic injection, picoinjection or lambda injection.

In some embodiments, the species includes a nucleic acid.

In some embodiments, the nucleic acid is clonal.

In some embodiments, the clonal nucleic acid arose from: encapsulating a single DNA molecule within a droplet; and then amplifying the DNA within the droplet.

In some embodiments, the methods further comprise characterizing the nucleic acid.

In some embodiments, characterizing comprises sequencing the nucleic acid.

In some embodiments, the methods further comprise identifying and quantifying genotypes based on the characterization of the nucleic acid.

In some embodiments, the methods further comprise sorting the rigidified droplet based on the characterization of the nucleic acid.

In some embodiments, the methods further comprise characterizing the sorted droplets.

In some embodiments, characterizing the sorted droplets comprises sequencing the nucleic acid.

In some embodiments, the method further comprises identifying and quantifying genotypes based on the characterization of the nucleic acid.

In some embodiments, the nucleic acid is DNA arising from amplification with one or more primers containing a functional group for covalent incorporation into the gel matrix via free radical chemistry during gel polymerization.

In some embodiments, the functional group is a 5' acrydite.

In some embodiments, the nucleic acid is DNA is amplified with one or more primers that either leave an overhang after DNA extension or are cleaved into an overhang.

In some embodiments, the primer comprises a target binding region and an overhang region, and where the overhang region comprises nucleic acid analogs.

In some embodiments, the nucleic acid analogs are LNAs or PNAs.

In some embodiments, the DNA is amplified with one or more tripartite primers comprising a 3' target binding region, a 5' attachment region that forms an overhang during polymerization, and a non-replicable region in between that blocks the polymerase from extending the overhang.

In some embodiments, the DNA concatemerizes at room temperature, with or without unions and blocks, and with or without restriction digestion and ligation, entrapping the DNA within the gel droplet.

In some embodiments, the species is a cell.

Another aspect of the invention is directed to a method of co-localizing clonal DNA comprising injecting into a droplet a bead attached to a hybridization capture agent complementary to a predetermined nucleic acid sequence, the droplet containing amplified DNA; and capturing the amplified DNA to the hybridization capture agent.

In some embodiments, the injection comprises any of the methods described herein.

In some embodiments, the methods further comprise characterizing the captured DNA.

In some embodiments, characterizing comprises sequencing the DNA.

In some embodiments, the methods further comprise identifying and quantifying genotypes based on the characterization of the nucleic acid.

Another aspect of the invention relates to a kit for genotyping variable DNA sequences comprising:
 a first hybridization probe complementary to a first predetermined sequence; and
 a second hybridization probe complementary to a second predetermined sequence;
 wherein the first predetermined sequence is a wild-type sequence of a conserved domain;
 the second predetermined sequence is a wild-type sequence including a suspected variable domain; and
 the first and second probes each have different detectable signatures.

In some embodiments, the detectable signatures of the first and second probe are selected from the following group: radioactive labeling, absorbence, phosphorescence, chemiluminescence, and fluorescence.

Another aspect of the invention relates to a method of genotyping variable DNA sequences comprising:
 providing a kit as described herein;
 providing target nucleic acids;
 hybridizing the first and second probes to the target nucleic acids;
 determining the presence or absence the detectable signature of each of the first and second probes; and
 inferring (a) the presence of the wild type DNA if both detectable signatures are detected, or (b) the presence of a mutation if only the detectable signature of the first probe is detected.

In some embodiments, the methods further comprise sequencing the DNA in order to identify the mutation if the presence of a mutation has been inferred.

In some embodiments, the disconnected fluid bridge contains a species and reactants for gel polymerization, the method further comprising entrapping the species within a gel in the droplet by gel polymerization of the reactants.

In some embodiments, the species is at least one of (a) a nucleic acid, and (b) a cell.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
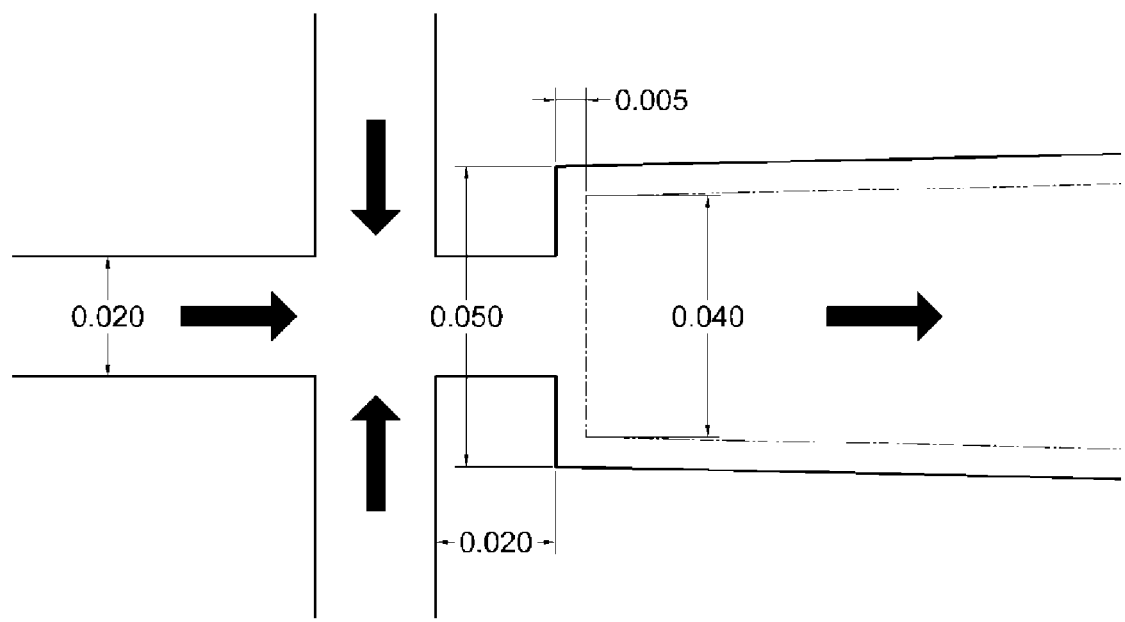

Having thus described the presently disclosed subject matter in general terms, reference will now be made to the accompanying Figures, which are not necessarily drawn to scale, and wherein:

FIG. 1 shows a microfluidic droplet generator with the step enhancement. Arrows indicate the direction of flow. (Solid line) 20 μm deep channels. (Dashed line) 50 μm deep channels. Units are in millimeters.

Figure 2:
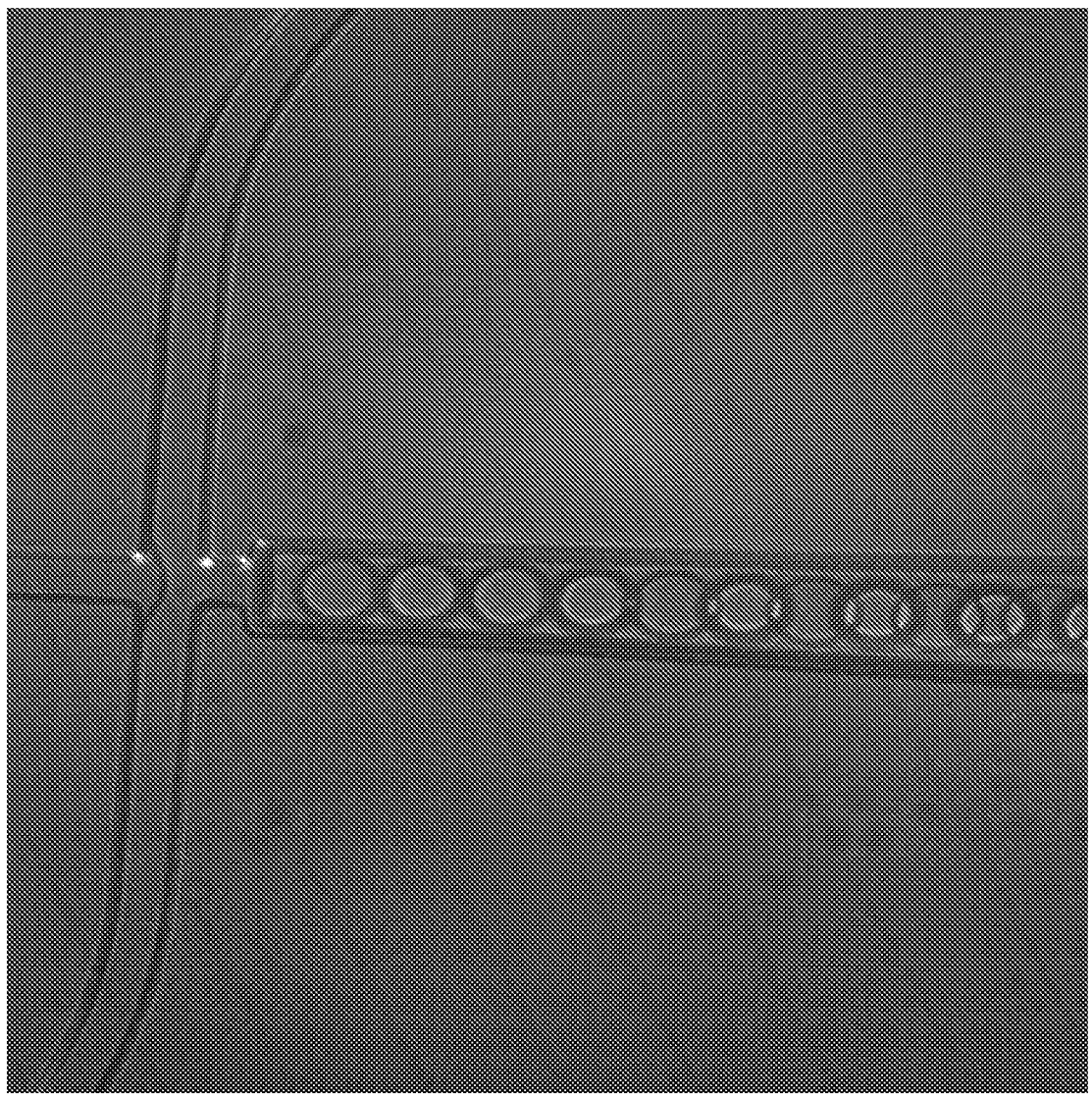

FIG. 2 shows a bridge-mode droplet generation with the step enhancement.

Figure 3:
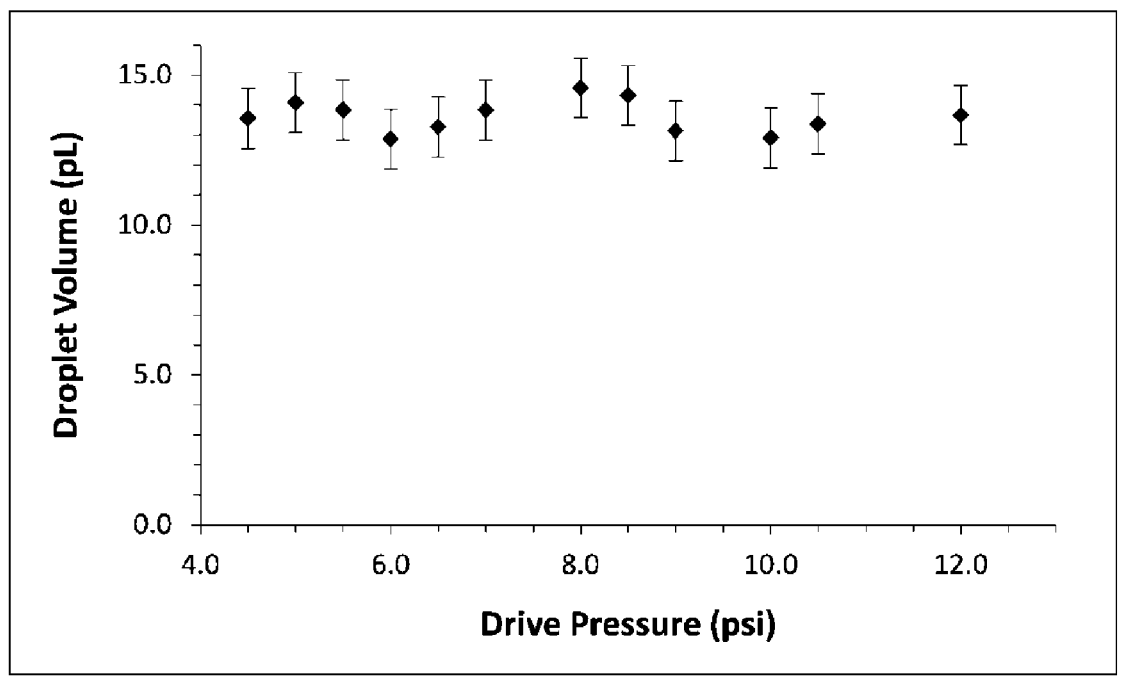

FIG. 3 shows droplet volume independence on drive pressure in bridge-mode with the step enhancement.

Figure 4:
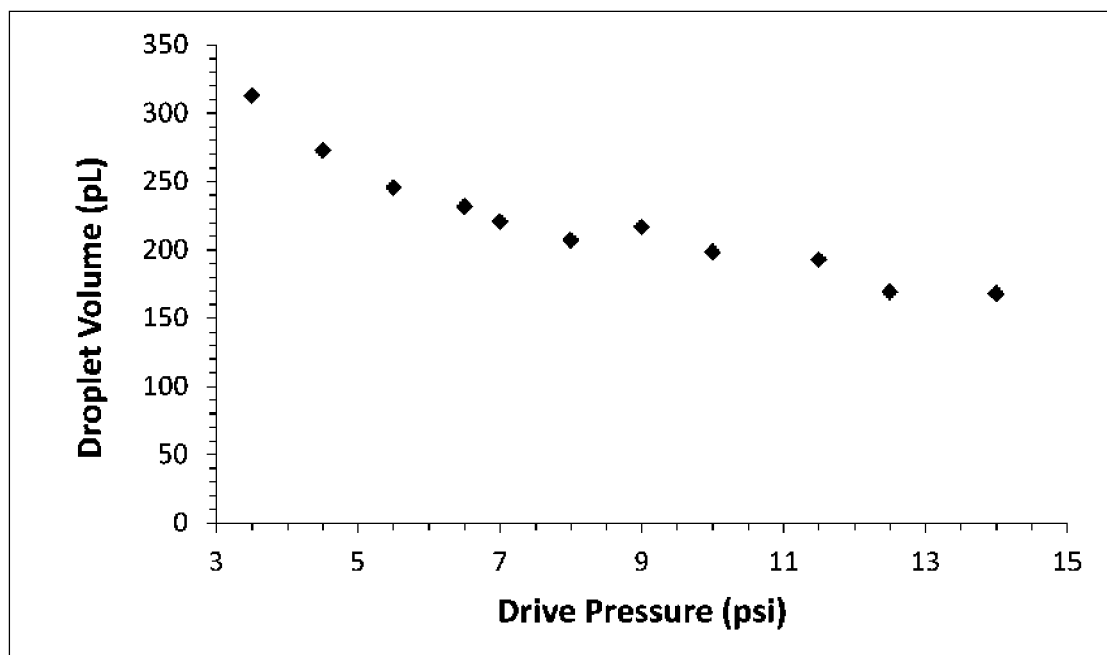

FIG. 4 shows droplet volume dependence on drive pressure in bridge-mode without the step enhancement.

Figure 5:
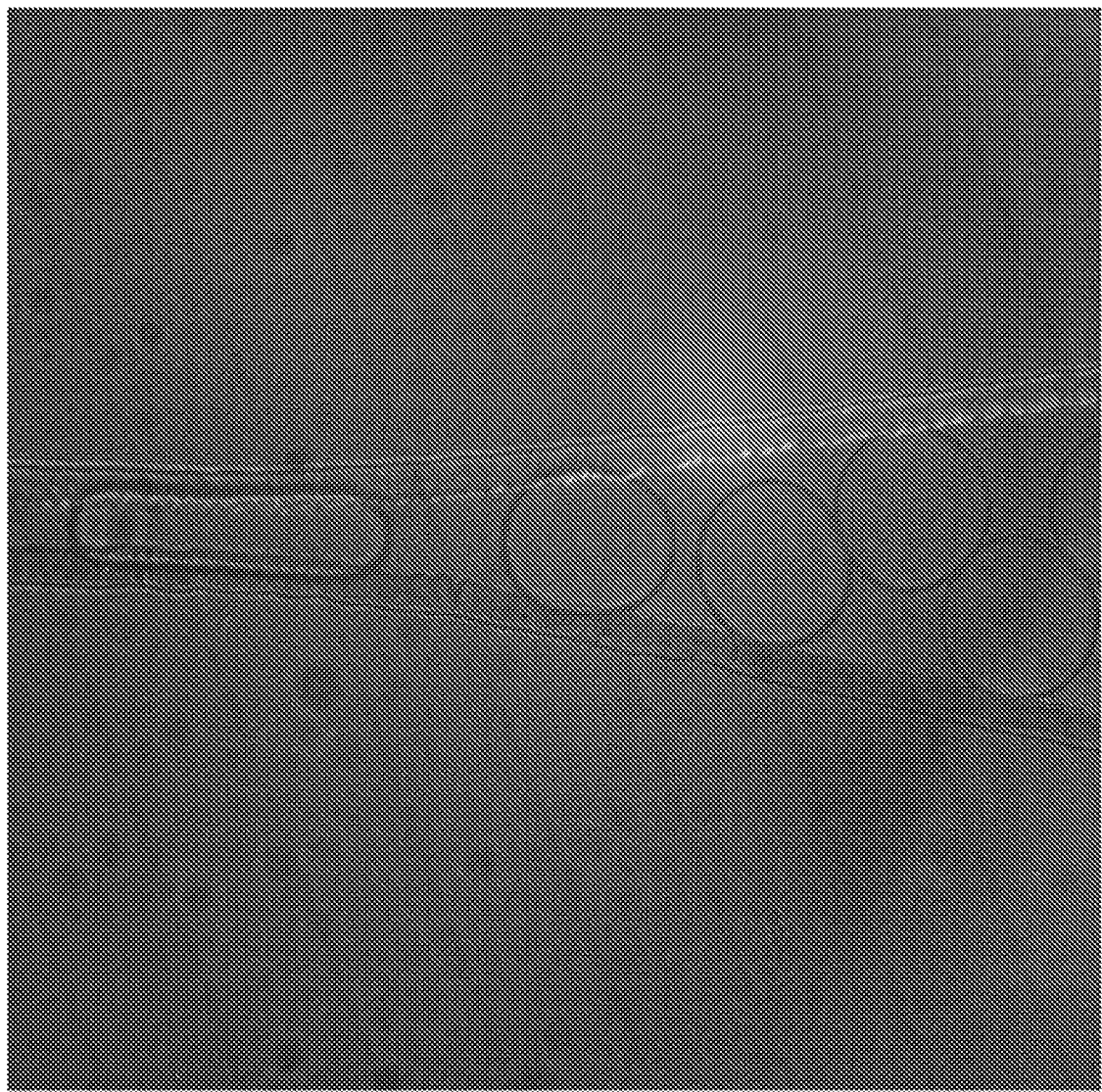

FIG. 5 shows a bridge-mode droplet generation without the step enhancement.

Figure 6:
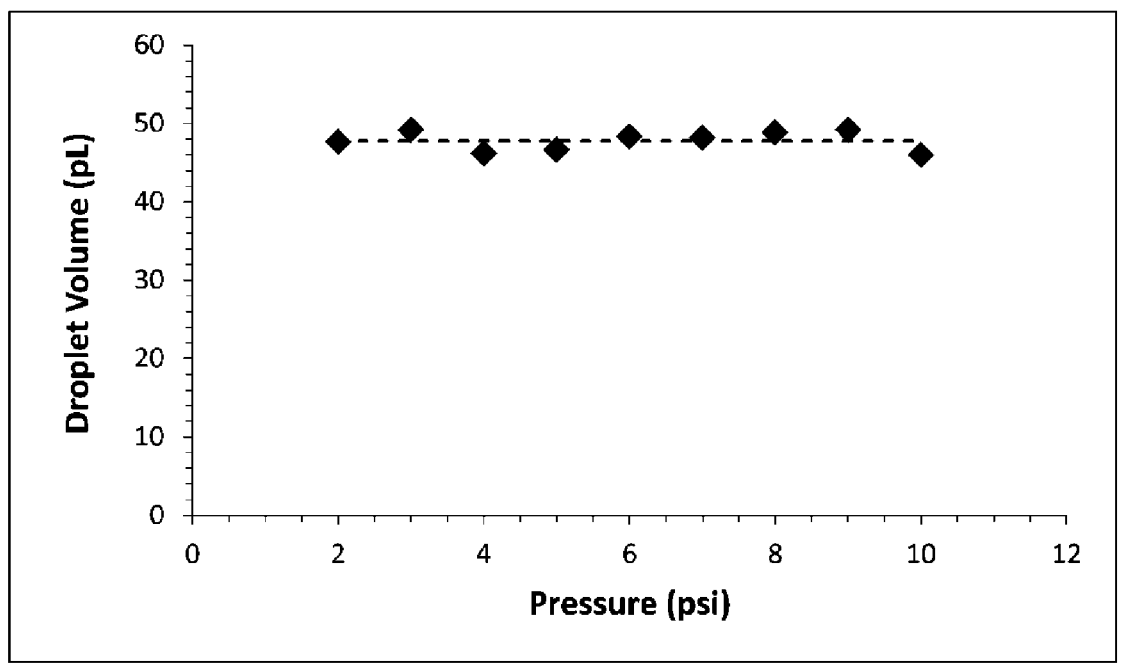

FIG. 6 shows a droplet volume independence on drive pressure in flow-focusing mode with the bridge enhancement.

Figure 7:
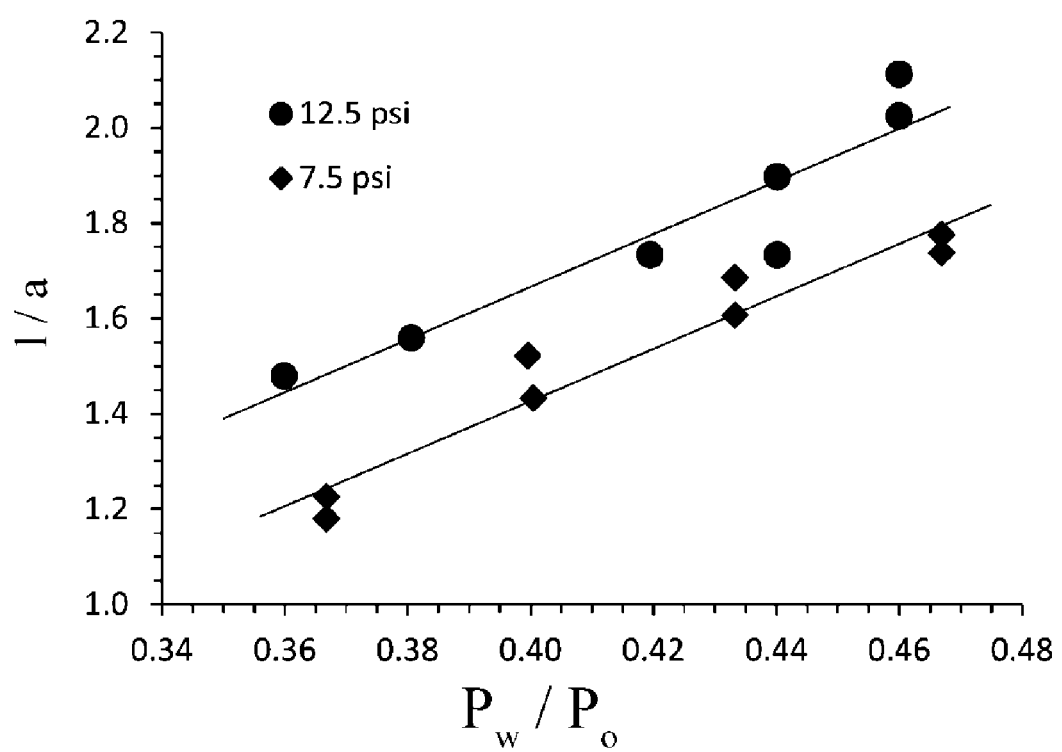

FIG. 7 shows a droplet volume dependence on drive pressure in flow-focusing mode without the step enhancement.

DETAILED DESCRIPTION

In the invention described here, the conventional need for feedback control is eliminated by a passive, open-loop approach using a novel microfluidic droplet generator with a step enhancement. The invented droplet generator yields uniform droplet volumes over a wide range of operating pressures, delivering robust performance at a very low cost. The invention also describes a method of droplet generation whereby the step enhancement improves the performance of any squeeze-mode or dripping-mode droplet generator, including but not limited to bridge-mode and flow-focusing configurations. The performance of the invention is sufficiently stable that it can be operated manually, such as with a bicycle pump, yet still delivering best-in-class microfluidic performance. Thus, not only does the invention greatly simplify and reduce the cost of operation in the laboratory, it opens the possibility of performing precision biology out in the field and off of the electrical grid.

FIG. 1 shows a droplet generator with a step enhancement, with arrows indicating the direction of flow. The three inlets channels (channels to the top, bottom, and left of the intersection in FIG. 1) are 20 µm wide and 20 µm deep, and comprise a traditional droplet generator. Such a droplet generator can be run in a variety of modes, including flow-focusing and bridge-modes.

In one non-limiting example, the device is run in bridge-mode (as described in PCT/US14/30346; herein incorporated by reference in its entirety). The aqueous fluids flow in opposed directions toward the intersection, and repeatedly form boluses of liquid that protrude into the oil-filled intersection. The boluses grow, collide, then merge together, and finally are snapped off into discrete droplets by the influence of the oil stream. Often the merge step is assisted electronically via a voltage applied to electrodes in fluid contact with the two aqueous phases (not shown in FIG. 1). In the conventional bridge-mode generator, the exit channel maintains the same characteristic width and height of the intersection. In the invented device, a step is introduced immediately downstream from the intersection (dashed line toward the right of the intersection in FIG. 1) that substantially improves the performance of droplet generation.

In another non-limiting example, the device is run in the flow-focusing mode that is well known by those of ordinary skill in the art. In flow-focusing mode, a single aqueous phase flows into the intersection from the channel to the left in FIG. 1, and oil fills the interection from opposed flows through the top and bottom channels in FIG. 1. Throughout this description, the invention is described in the context of these two examples, however many droplet generators are known to those of ordinary skill in the art, including, but not limited to, head-on, T-junction, Y-junction, double T-junction, K-junction, V-junction, and co-flow configurations. The step enhancement may improve the performance of any droplet generator.

The step feature in FIG. 1 is located immediately downstream from the droplet generator (20 µm), and it increases the channel height from 20 to 50 µm. Without wishing to be bound by any theory, the abrupt drop in capillary pressure arising from the sudden increase in channel depth introduces a geometry-dependent droplet snap-off influenced by surface tension. Without the step enhancement, droplet snap-off is generally driven by viscous forces and localized pressure fluctuations that depend on the flow-rate. Thus, the step enhancement shifts the balance of forces that drive snap-off from those that are susceptible to imperfect flow or pressure sources to those that depend on channel geometry, substantially stabilizing device performance.

The invention bears some similarity to "step emulsification", the process of generating droplets by flowing a continuous stream of the dispersed phase into the continuous phase over an abrupt or gradual expansion in channel height. The distinguishing feature that differentiates the invention from step emulsification is that the dispersed phase is already urged into a strained, pre-snap configuration prior to encountering the step. Benefits of the invention over step emulsification include the ability to monitor droplet generation electronically, as described below, as well as combining the high-throughput of squeezing and dripping mode devices with the stabile, geometry-dependent performance of step emulsifiers.

One step emulsifier has been described (Chan, E. M., Alivisatos, A. P., and Mathies, R. A., 2005, *J. Am. Chem. Soc.*, 127(40), 13854-13861) that contains the features described in FIG. 1: a flow-focusing structure with a downstream step. The authors reported a method of droplet generation whereby the dispersed phase was focused hydrodynamically into a narrow streamline (also known as jetting) that was dispersed into droplets over the step of the device. In essence, this device triggered the spontaneous breakup of a narrow stream that had not yet deformed or dispersed due to Rayleigh-Plateau instability. In all methods of the invention, the discriminating feature over the method from Chan et al. is that the dispersed phase has already been urged into a pre-snap configuration by the upstream structures. The device of the invention is also substantially different from the device of Chan et al. The microfluidic device of FIG. 1 is configured for bridge-mode operation, and the distinguishing feature is that two electrochemical electrodes are positioned in direct electrical contact with the dispersed phase for injection of electrical current into the microfluidic intersection. As described in (PCT/US14/30346; herein incorporated by reference in its entirety), electrical current is used in the invented device to manipulate and to monitor droplets, both a feature and a capability absent in prior work with step emulsification. The ability to monitor droplets electrically offers many improvements over existing techniques, including but not limited to low cost, miniaturized replacement of expensive and bulky optical systems, and compatibility with opaque materials.

The step feature described above is not intended to be a limiting example. Those of ordinary skill in the art will recognize that the benefit of the step can be achieved with various geometries, including but not limited to varying distances of the step from the intersection, varying channel heights, varying orientations (step up, step down, step sideways, steps in multiple directions, or multiple steps in staggered positions), and varying slopes of the step. The invention considers all geometries that result in a sufficiently sudden decline in capillary pressure to shift the balance of forces that drive droplet snap-off.

The invention has been described thus far in the context of droplet generation, but in addition, droplet injection is also considered. Applications, such as analyses of genomic expression in single-cells, employ droplet-by-droplet fluidic injections, and they have the same stringent requirements for precise and accurate formulation as do applications for droplet generation. In the device of the invention, the upstream continuous phase is also envisioned to contain a stream of droplets, separated by oil, that impinge on the intersection at regular intervals such that the fluidic bridge formed within the intersection comprises the upstream droplet and some amount of fluid from each side channel. Once the bridge forms, the dynamics of snap-off are substantially similar to the case of bridge-mode droplet generation and the same benefits of the invention apply. Furthermore, improvements in the uniformity of droplet injection by methods other than bridge-mode injection are considered. Various injection methods are well known to those practiced in the art, including microfluidic injection, picoinjection, or lambda injection, and each is envisioned to benefit from the methods of the invention.

EXEMPLIFICATIONS

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Device

FIG. 2 shows droplets generated by the invented device. The microfluidic chip of design from FIG. 1 was fabricated by standard soft lithography, plasma bonded to a glass cover slide, and silanized to provide hydrophobic channel surfaces. The oil phase contained HFE 7500 (3M) and a fluorosurfactant (RAN Biotechnologies). The aqueous phase contained 1×TE buffer (pH 8.0) and 1 M NaCl. Electrodes in contact with the aqueous phases, in pressurized off-chip sample reservoirs, were poised at 30 V to assist merging and monitor droplet generation. Flow was driven with the same pressure applied to all of the inlet reservoirs simultaneously, ensuring proportional changes to flow rate. FIG. 2 shows a stream of droplets generated downstream from the intersection. Droplet volumes were measured at a variety of different drive pressures from their diameters in high speed images like FIG. 2. Image pixels were converted to distance in microns using a known calibration feature on the chip. The small baseline uncertainty in the overall volume measurement arose from image-to-image variations in this pixel calibration (2% CV).

FIG. 3 shows that droplet volumes were invariant to pressure changes over a wide range (~3×). Error bars indicate the baseline uncertainty from image analysis, and within the error, the droplet volumes do not change with pressure. Additionally, no apparent trend appeared; the pressure-to-pressure variations seemed random. The overall CV on droplet volume throughout this extended run was 4%. Thus open-loop operation of the invented device delivers performance equivalent to or better than existing feedback-controlled systems. FIG. 4 shows the same demonstration with a bridge-mode generator that lacked the step enhancement. Over a similar 4-fold increase in drive pressure, the droplet volume was halved. In conclusion, the step enhancement substantially improves the stability of droplet generation in bridge-mode operation.

The device of the invention employs bridge-mode droplet generation to achieve electrical measurements by electrical continuity measurements. In our hands, bridge-mode droplet generation is restricted to the squeezing mode of droplet generation, a process generally characterized by the droplet bolus extending to the boundaries of the channels and becoming squeezed in the direction of flow by a local increase in pressure until it snaps off. Without wishing to be bound by any theory, it stands to reason that the bridge-mode generator would be limited to squeezing mode because the dispersed phases must first stretch halfway across the channel to form a bridge, a process that perhaps would be impeded at the higher fluid strain rates leading to the dripping mode of droplet generation. Dripping mode is generally a more desirable, higher performance mode of droplet generation, yielding smaller droplets at higher frequencies, but we have never achieved dripping mode performance with a simple bridge-mode generator. FIG. 5 shows a droplet emerging from the exit of a bridge-mode generator without the step enhancement. Clearly the droplet is a slug-like conformation, indicative of squeeze mode snap-off. Hence a down-side of simple bridge-mode droplet generation is the inability to generate droplets at the same high frequencies achieved in similar geometries with flow-focusing generators running in dripping mode. However, the step enhancement eliminates this disadvantage of bridge-mode generation. In this demonstration, the cross-shaped intersections were nominally the same with and without the step enhancement. Comparing the droplet volumes in FIG. 4 to FIG. 3 reveals a dramatic 10-fold reduction in the size of the droplets (from 100 s to 10 s of picoliters) due to the step enhancement. Therefore, in addition to the substantial benefit of robust operation, the step enhancement also brings a special benefit to bridge-mode operation: it reduces the size of the droplets, and consequently boosts generation frequencies to levels on par with dripping mode generators.

Example 2

Method

The same microfluidic chip as above, from FIG. 1, was run in flow-focusing mode to demonstrate the benefit of the method of the invention for all droplet generators. With the same materials, same instrument, same data analysis, and same pressure scheme as above, droplet volumes were measured as a function of changing pressure. FIG. 6 shows that over a 5-fold change in pressure the droplet sizes were invariant within our ability measure. By-eye comparison to the horizontal trendline reveals no discernible pattern other than random fluctuations, likely artifacts of the measurement. The coefficient-of-variation of droplet volume was 3% over the range studied, a performance as good as the best expected from instruments with vision systems and feedback control.

Within the field there is some residual expectation from early studies in droplet dynamics that performance such as described here naturally arises from our use of the same pressure on each drive line. As the argument goes, if the pressures change proportionally, so do the flow rates, and within a first-order of approximation the sizes of the droplets will scale according to some power of the ratio of the flow rates. For example, Ward et al. (Ward, T., Faivre, M., Abkarian, M., and Stone, H. A., 2005, *Electrophoresis*, 26, 3716-3724) concluded that the droplet diameter scales as the square of the ratio of the aqueous-to-oil pressures in a flow focusing device. Of course we agree with the consensus regarding scaling laws, however the original data that supports the scaling laws was analyzed to elucidate the underlying principles in fluid mechanics, not to assess the value of the performance for precision biology.

Here we revisit some of the original published data on droplet scaling to reveal that substantial droplet size variations with pressure, even at constant ratios, have always been observed when considered at the level of accuracy required for applications such as droplet digital PCR. FIG. 7 shows a subset of the data from Ward et al. that was originally used to derive the pressure scaling law, where l/a on the y-axis is a dimensionless representation of the droplet diameter, and $P_w/P_o$ on the x-axis is the ratio of the drive pressures for water and oil. Droplet diameters were measured at multiple pressures (excerpted here at 7.5 and 12.5 psi oil pressure) for each ratio studied. Thus, for the purpose of evaluating the droplet size uniformity at a fixed ratio, such as the 1:1 ratio used in the examples of the invention above, the distribution of droplet sizes along the vertical lines in FIG. 7 should be examined. Solely for the crude purpose estimating performance expectations, the data was extracted from the original work by a graphical approach and fitted by chi square minimization to a pair of trendlines simultaneously for each pressure, 7.5 and 12.5 psi. The trendlines were constrained to be parallel. With trendlines to guide the eye, it is clear from FIG. 7 that the droplets observed at 12.5 psi were all larger than the droplets observed at 7.5 psi when generated at the same ratio of pressures. This is a second-order effect from the perspective of the scaling laws, but these small differences have emerged as critically important for proper engineering of robust microfluidic devices for current biological applications. To estimate the droplet volume variation, the ratio of the trendlines taken at a pressure ratio of 0.42 is 1.2, translating to a volume increase of ~70%. This amounts to at least a 20× increase in variation compared to the results of the method of the invention, and over a 3× smaller range of pressures.

In conclusion, the scale of droplet size variation that we observed in FIG. 4 for the bridge-mode droplet generator is similar to variations observed by others previously for flow-focusing generators. In both cases the variations were greatly attenuated by the method of the invention. Furthermore, since the underlying fluid mechanics of droplet snap-off are similar across all droplet generators, we anticipate that the method of the invention has broad usage beyond two configurations analyzed here.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method comprising:
providing a system, the system comprising a substrate that defines microfluidic channels including:
a main channel having a main input in fluid communication with a main output, the main channel defining an intersection site along a path of fluid flow from the main input to the main output;
a first side channel having a first side input in fluid communication with a first side output, the first side output being in fluid communication with the main channel at the intersection site;
a second side channel having a second side input in fluid communication a second side output, the second side output being in fluid communication with the main channel at the intersection site;
a first electrode located so as to be in electrical contact with the first side channel fluid when the first side channel has been charged with the first side channel fluid; and
a second electrode located so as to be in electrical contact with the second side channel fluid when the second side channel has been charged with the second side channel fluid;
charging the main channel with a main channel fluid from the main input;
charging the first side channel with a first side channel fluid from the first side input, the first side channel fluid being immiscible with at least a first component of the main channel fluid;
charging the second side channel with a second side channel fluid from the second side input such that the first and second side channels are separated from one another by the main channel fluid, the second side channel fluid being immiscible with at least the first component of the main channel fluid;
flowing the main channel fluid from the main channel input to the main channel output and through the intersection point;
allowing electrical current to flow through the intersection;
connecting the first and second side channel fluids with a fluid bridge at the intersection point;
straining the fluid bridge within the main channel fluid such that the fluid bridge encounters at least one enhancement channel located downstream, within, or adjacent to the intersection site;
flowing the fluid bridge into the at least one enhancement channel, wherein said enhancement channel causes an abrupt drop in capillary pressure to thereby improve stability of droplet generation; and
disconnecting the fluid bridge from the first and second side channel fluids yielding a droplet and separating the first and second side channel fluids by the first component of the main channel fluid.

2. The method of claim 1 wherein the fluid bridge consists of a second component of the main channel fluid, wherein the second component is a dispersed aqueous droplet.

3. The method of claim 1 wherein connecting the first and second side channel fluids with the fluid bridge comprises forming an electrically conductive connection between the first and second side channel fluids.

4. The method of claim 1 wherein the system further comprises a voltage source connected to both the first electrode and the second electrode.

5. The method of claim 1 wherein:
the first electrode is located within the first side channel; and
the second electrode is located within the second side channel.

6. The method of claim 1 wherein the first side channel fluid, the second side channel fluid and the fluid bridge are all aqueous.

7. The method of claim 1 wherein the first component of the main channel fluid is an oil.

8. The method of claim 1 wherein the fluid bridge consists essentially of the first and second side channel fluids, and contains substantially none of the first component of the main channel fluid.

9. The method of claim 8 wherein connecting the first and second side channel fluids with a fluid bridge comprises extending the first and second side channel fluids into the intersection site so that the first and second fluids come into contact, thereby forming the fluid bridge.

10. The method of claim 9 wherein disconnecting the fluid bridge from the first and second side channel fluids creates a droplet consisting essentially of the first and second side channel fluids.

11. The method of claim 10 wherein:
the system further comprises a current meter operably connected to the first and second electrodes so as to be capable of measuring the current between the first and second electrodes as a function of time; and
the method further comprises recording the current measured by the current meter as a function of time.

12. The method of claim 1 wherein:
the fluid bridge is a second component of the main channel fluid; and
flowing the main channel fluid comprises flowing the fluid bridge from the main channel input to the intersection point and from the intersection point to the main channel output.

13. The method of claim 12 wherein:
the system further comprises a current meter operably connected to the first and second electrodes so as to be capable of measuring the current between the first and second electrodes as a function of time; and
the method further comprises recording the current measured by the current meter as a function of time.

14. The method of claim 1 wherein:
connecting the first and second side channel fluids with the fluid bridge comprises incorporating at least some of the first and/or second side channel fluids into the fluid bridge; and
disconnecting the fluid bridge comprises retaining in the resulting droplet the incorporated at least some of the first and/or second side channel fluids.

15. The method of claim 1, wherein said at least one enhancement channel distance to intersection channel width comprises a step offset ratio of 0, 0.1, 0.2, 0.5, 1.0, 2.0, 3.0, 4.0, or 5.0.

16. The method of claim 1, wherein said at least one enhancement channel comprises a channel height that is larger than the intersection channel height.

17. The method of claim 1, wherein said at least one enhancement channel comprises a channel height that is 0.5×, 1×, 1.5×, 2×, 2.5×, 3×, 3.5×, 4×, 4.5×, and 5× larger than the intersection channel height.

18. A method comprising:
providing a system, the system comprising a substrate that defines microfluidic channels including:
an intersection site comprising a microfluidic droplet generator;
a first channel or set of channels having at least a first input in fluid communication with the intersection site;
a second channel or set of channels having at least a second input in fluid communication with the intersection site;
an exit channel or channels having an exit output in fluid communication with the intersection site;
charging the first channel or set of channels with at least a first channel fluid;
charging the second channel or set of channels with at least a second channel fluid, the first channel fluid being immiscible with the second channel fluid;
flowing the first channel fluid from the first channel input into the intersection site, and flowing the second channel fluid from the second channel input into the intersection site;
urging the first channel fluid into a strained pre-droplet by means of squeeze-mode or dripping-mode droplet generation within or downstream of the intersection site;
flowing the pre-droplet into at least one enhancement channel located downstream, within, or adjacent to the intersection site, wherein said enhancement channel causes an abrupt drop in capillary pressure to thereby improve stability of droplet generation; and
disconnecting the pre-droplet from the first channel fluid yielding a droplet.

19. The method of claim 18, wherein the first channel fluid is aqueous and the second channel fluid is an oil.

20. The method of claim 18, wherein the intersection site comprises a flow-focusing, head-on, T-junction, Y-junction, double T-junction, K-junction, V-junction, or co-flow droplet generators.

* * * * *